(12) United States Patent
Schultheiss

(10) Patent No.: US 7,390,308 B2
(45) Date of Patent: Jun. 24, 2008

(54) APPARATUS AND PROCESS FOR OPTIMIZED ELECTRO-HYDRAULIC PRESSURE PULSE GENERATION

(75) Inventor: Reiner Schultheiss, Illighausen (CH)

(73) Assignee: General Patent, LLC., Mariezza, GA (US)

( * ) Notice: Subject to any disclaimer, the term of this patent is extended or adjusted under 35 U.S.C. 154(b) by 750 days.

(21) Appl. No.: 10/798,506

(22) Filed: Mar. 12, 2004

(65) Prior Publication Data

US 2005/0113722 A1    May 26, 2005

(30) Foreign Application Priority Data

Mar. 14, 2003    (DE)    ................. 103 11 659

(51) Int. Cl.
  *A61H 1/00*    (2006.01)
  *C12N 13/00*    (2006.01)
(52) U.S. Cl. .......................... 601/4; 435/173.6
(58) Field of Classification Search ............ 601/2–4; 435/173.6
  See application file for complete search history.

(56) References Cited

U.S. PATENT DOCUMENTS

| | | | |
|---|---|---|---|
| 4,085,170 A * | 4/1978 | Simpson et al. ............. | 261/1 |
| 5,105,801 A | 4/1992 | Cathignol et al. | |
| 5,208,788 A * | 5/1993 | Dancer et al. ............. | 367/147 |
| 5,425,570 A | 6/1995 | Wilkinson | |
| 6,217,531 B1 | 4/2001 | Reitmajer | |

FOREIGN PATENT DOCUMENTS

| | | |
|---|---|---|
| DE | 3929457 A1 | 10/1990 |
| EP | 911 804 A2 | 4/1999 |

OTHER PUBLICATIONS

G. Weimar, Hochgeschwindigkeitsbearbeitung II, Umformung von Blech durch Druckwellen, Werkstatt und Betrieb, 96. Jahrgang, 1963, Heft 5, S 293-305.

* cited by examiner

*Primary Examiner*—Eric F. Winakur
*Assistant Examiner*—Michael Rozanski
(74) *Attorney, Agent, or Firm*—David L King

(57) ABSTRACT

The invention relates to an apparatus and a process for optimized electro-hydraulic pressure pulse generation that records characteristic parameters which can be measured insusceptible to error and compared with set values. The object of the invention is achieved by an apparatus in which an electro-hydraulic shock wave system is provided with a measuring and control device (13*a*, 13*b*) that measures the discharge current between the electrode tips (4, 5), and a process that influences the system parameters by means of the apparatus.

35 Claims, 3 Drawing Sheets

APPARATUS AND PROCESS FOR OPTIMIZED ELECTRO-HYDRAULIC PRESSURE PULSE GENERATION

This application claims priority from German Patent Application DE 103 11 659.1, filed Mar. 14, 2003, whose contents are incorporated herein by reference in its entirety.

The invention relates to an apparatus and a process for optimized electro-hydraulic pressure pulse generation.

BACKGROUND OF THE INVENTION

Electro-hydraulic shock wave systems are used to generate pressure pulses by applying voltage by means of an RLC discharge circuit between two electrodes located in a fluid, causing a plasma to form between the electrodes during the discharge, generating a shock wave.

The properties of the shock wave depend significantly on the discharge current and the charging voltage. These, in turn, result from the parameters of the RLC circuit, the applied voltage and the geometry of the electrode configuration.

Document DE 40 20 770 elucidates the characteristic of the discharge curves of current and voltage, Conventional systems make use of a damped oscillation.

The breakdown of the discharge voltage between the tips of the electrodes, which usually are located in an aqueous solution, is a statistical effect, since local physical conditions of the electrical field and the inhomogeneities of the medium located between the tips cause extreme variations in the formation of the electric arc and of the plasma. The reproducibility of the discharge is made more difficult by the fact that the electrode tips wear out after many discharges, which not only alters the surface roughness, but also increases the distance between the electrodes due to loss of material in the tips. In the course of time, this results in an increase in the minimum voltage, which is necessary in order to achieve a breakdown.

From DE 40 20 770 it is known that this problem can be countered by using a highly conductive electrolyte as the fluid in which the electrodes are located. The discharge then becomes a type that is critically damped, in which the latency time, i.e. the time until the breakdown, is more or less completely suppressed, since the electrical energy is converted directly to form a vapor bubble and therefore a pressure wave, so that the formation of a plasma does not even come about.

However, this apparatus requires a very careful control of the electrode distance, since the system reacts very sensitively to this distance.

Another procedure is depicted in EP 0911 804. This document describes an apparatus that measures the directly controlled distance, i.e. voltage and its gradient, and varies the distance between the electrodes based on deviation from a set voltage. The set value is defined so that when it is reached the optimum conversion of electrical energy into pressure energy takes place. The increase in distance between the electrode tips can therefore be corrected, increasing the life of the electrodes. The individual shock waves are more similar to each other, because they are generated at least with equivalent electrode geometry. Depending on whether a constant or a variable reference value is used, the electrode distance can be increased or decreased.

However, voltage measurement in a high-voltage discharge circuit is difficult to implement. Interference causes very high proneness to errors.

The object of the invention is to present an apparatus and a process for optimized electro-hydraulic pressure pulse generation that records characteristic parameters which can be measured insusceptible to error and compared with set values. A voltage measurement alone furthermore enables no conclusion about the energy conversion between the electrodes.

The object of the invention is achieved by an apparatus in which an electro-hydraulic shock wave system is provided with a measuring and control device that measures the discharge current between the electrode tips, and a process that influences the system parameters by means of the apparatus.

SUMMARY OF THE INVENTION

The discharge current displays a certain phase shift as compared with the discharge voltage. It does not reach the maximum value until the discharge voltage has dropped drastically. The latency time is the time of the current curve, within which practically no current flows despite applied voltage. During this time, the input energy is reduced by means of the ohmic resistance of the aqueous medium, and initial pre-discharge channels are also formed between the tips of the electrodes. But the electrical breakdown does not occur until a plasma channel is formed, so that a pressure wave can form around the spark channel. The discharge process has the form of a damped oscillation, whereby the damping is defined by the parameters of resistances, capacities and inductivities, and also by the geometry of the electrodes. The system oscillates until the electrical energy that is stored in the discharge condenser has been fully converted into the pressure pulse, into light, into excited states, into heat, etc. The pressure pulse is generated, however, only during the first discharge, i.e. until the second zero crossing of the current curve. The system therefore must be designed so as to prevent further oscillations to the greatest extent possible, i.e. it must operate in or near the aperiodic borderline case.

Standard devices for measuring current can be used as the measuring equipment, such as a Rogowski coil, a shunt or some other state-of-the-art measuring device.

The results of the current measurement can be used at any time to check whether the generation of the pressure pulses is still taking place in the selected oscillation range and if this is not the case, it is possible to influence the configurable parameters.

In an advantageous further embodiment, the measuring and control device measures not only the current, but also the discharge voltage. The existence of both measuring curves reduces the proneness to errors from external sources of interference and enables the calculation of further values for analysis, such as the generated energy at a particular point in time.

In another advantageous further embodiment, the measuring and control device directly measures the discharge output, preferably by means of a combined current and voltage measurement. In the optimum working range, power is converted only during the first electromagnetic oscillation.

In yet another advantageous further embodiment of the apparatus, the measuring and control device compares at least one measuring or control value with a least one set value. The set value or values, for example the latency time, a maximum current value, a specified output value at a specified time or a specified current curve are defined by an initial optimum system setting or by a random pre-selection, which is based on theoretical calculations or previous measurements. The measuring and control device indicates the deviation or the degree of deviation of the measured values from the set value or values.

However, the set values can also be relative values. For example, the parameters of the RLC circuit and of the electrode distance are initially such that an aperiodic discharge takes place. Then, with all further discharges, it should be ensured that the second current maximum has an absolute value, which is less than one-fourth the first current maximum. In this case, the set value is a value determined based on the first measured value. The set value must then not be re-defined for each desired change in parameters, e.g. for the selection of a different discharge voltage.

As a further possibility, the comparison can be made with a combination of set values. First, it is determined whether the first current amplitude is even sufficient to generate a spark, and in a second comparison, whether the second maximum is small enough so that the discharge takes place near the aperiodic borderline case.

Since the discharge process is a statistical process, it may be useful to average the measured values from several discharges and to compare this mean value with the set value or values.

In a further advantageous embodiment of the apparatus, the distance between the electrodes is variable. If the deviation from the set values is too great, or if the measured values no longer correspond to a desired profile, then the distance between the electrodes can be altered in order to achieve a different discharge range. To do this, either both electrodes can change their position, or one electrode can be moved in relation to the other electrode. In a shock wave focused by reflection, however, the gap between the electrodes should remain in the focal point, if possible.

The electrodes are moved by means of actuating elements. These are operated by means of a motor with a transmission, a servo motor, a piezo-ceramic drive, an inductive magnet, a hydraulic element, a pneumatic element or some other known drive mechanism.

In a preferred embodiment of the invention, in case of deviation of at least one measured or control value from at least one set value or in case of deviation of measured and control value curves from set value curves, the measuring and control device corrects the electrode distance, therefore automatically influencing the discharge characteristic.

The wear on the electrodes can, for example, be countered by holding one electrode in its position so that it can be moved by a motor and the distance between the electrodes is kept as constant as possible. This is enabled by the apparatus according to the invention without direct measurement of the distance, namely by controlling the discharge characteristic.

The ability to adjust the electrode distance requires complex technical means, namely the entire actuating unit for moving at least one electrode. If the electrodes are not made of a fully guidable wire, then the life of the electrodes is limited anyway and replacement of the electrodes is inevitable. Therefore, a preferred embodiment of the apparatus according to the invention, in case of deviation of at least one measured or control value from at least one set value or in case of deviation of measured and control value curves from set value curves, enables the measuring and control device to correct the charging voltage. As the electrode distance becomes larger due to wear, the charging voltage must be increased accordingly in order to ensure a consistent discharge characteristic.

The apparatus can be used not only to ensure the consistent quality of a system setting that has been selected, but also to start a shock wave generation system. For this purpose, the set values are defined arbitrarily by the operator, and the manipulated variables are varied by the measuring and control device until the system is within the desired working range.

The described apparatuses according to the invention preferably are used for the extra-corporeal disintegration of concretions in human beings and mammals or for the extra-corporeal treatment of all other tissues in human beings and mammals. Especially when an electro-hydraulic shock wave unit is to be used successively with one set of electrodes in different treatment areas, the generated shock waves must be adjustable. This adjustment can be carried out by means of the discharge characteristic. In a treatment at one treatment location, the characteristic should remain as constant as possible, which can be ensured by use of the apparatus according to the invention.

A process for the generation of optimized pressure pulses in electro-hydraulic shock wave systems is characterized by the following process steps:

a) Setting of the RLC circuit and of the electrode distance in an electro-hydraulic shock wave system to selected initial parameters, b) Initiation of the discharging process, c) Determination of the discharge current and at least one measured value by a measuring and control device, d) Comparison with at least one set value, e) Correction of a system parameter, e.g. of the applied charging voltage or of the electrode distance, by a correction increment based on the deviation from the set value, f) Further with b)

This process is particularly advantageous because the system parameters change only minimally with each shock wave generation, a correction can be made after each discharge and, fox each treatment the total number of discharges released is able to stabilize the system due to successive execution of the process. Therefore, it is not necessary to conduct "test discharges" solely for the purpose of configuring the system; instead, optimization takes place during normal operation.

In an alternative process the measured values are collected for several discharges and averaged, before they are compared with one or more set values.

Further advantageous embodiments will be apparent from the following description and from the claims.

DETAILED DESCRIPTION OF EXEMPLARY EMBODIMENTS

Figure 1A:
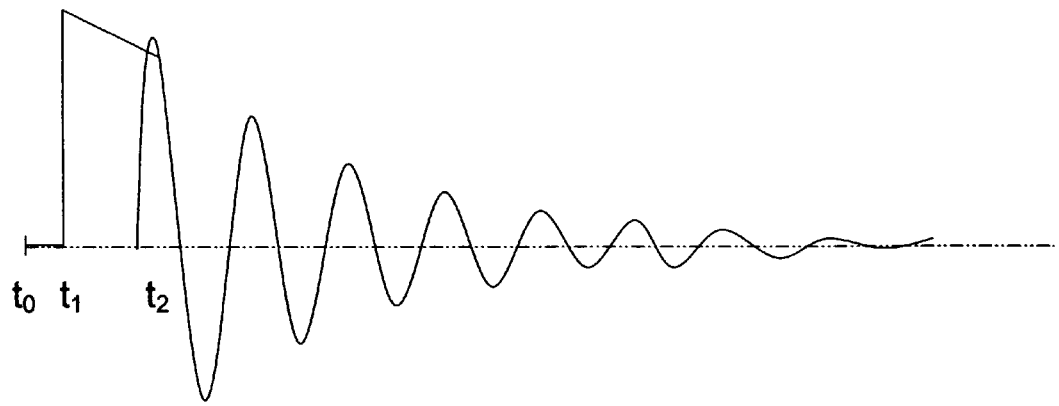
FIG. 1a a simplified depiction of the voltage curve between the electrodes during a damped oscillation.

FIG. 1a shows a simplified depiction of the voltage curve between the electrodes during a damped oscillation. After an initial time t1 the maximum voltage is applied between the electrodes. Until a time t2, the ignition delay or latency time, the path between the electrodes is already slightly conductive, since electrolysis is already beginning and the ohmic resistance is reduced through input energy. Further processes, such as the formation of initial pre-discharge channels, also take place. After the time t2 the electric breakdown begins, the plasma channel forms and a pressure wave develops around the spark channel. The voltage breaks down very quickly and the discharge condensation discharges in a damped oscillation, with damping parameters defined by the electrode distance, the medium between the electrodes and the RLC circuit.

Figure 1B:
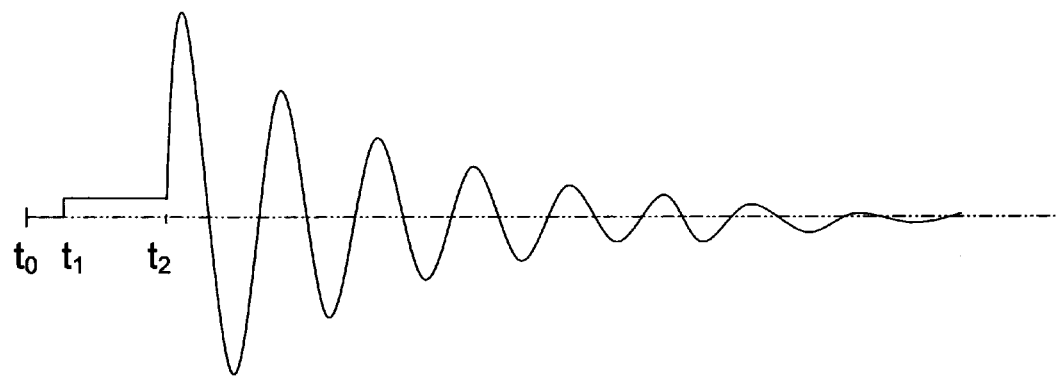
FIG. 1b a simplified depiction of the current curve between the electrodes during a damped oscillation.

FIG. 1b shows the corresponding current curve. During the latency time the discharge current between the electrodes is very low. As soon as the electrical breakdown begins at the t2, the actual flow of current between the electrodes begins. The oscillation reversal continues until the electrical energy that was stored in the discharge condenser is fully converted into other forms of energy.

The pressure pulse, however, is formed only during the time of the first discharge before the second zero crossing of the current at the time t3. A system for pressure pulse generation must therefore be operated so that the majority of the applied energy is converted by this time.

Figure 2A:
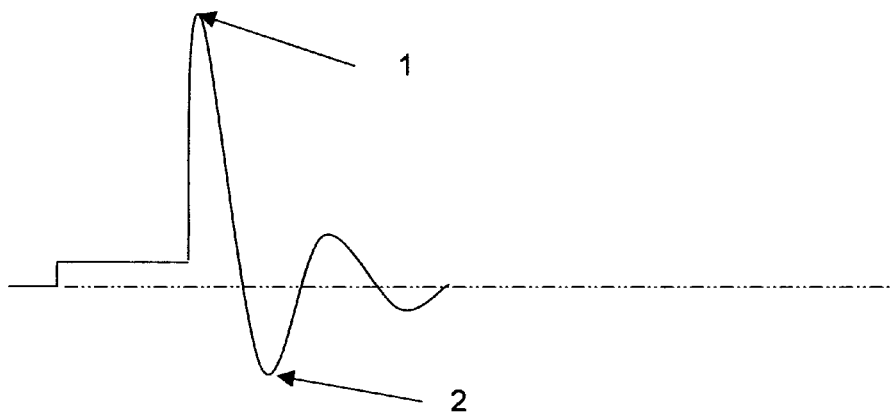
FIG. 2a a simplified depiction of the current curve in the proximity of the aperiodic borderline case.

FIG. 2a shows a simplified depiction of the current curve in the proximity of the aperiodic borderline case. In order to even achieve a breakdown, the first current maximum 1 should reach a minimum value, which can be defined as a set value. Good utilization of energy can then be achieved, when the absolute value of the second maximum 2 is less than 25% of the first maximum value 1.

Figure 2B:
FIG. 2b a simplified depiction of the current curve in the aperiodic borderline case.

The optimum conditions exist in the aperiodic borderline case. FIG. 2b shows a simplified depiction of the current curve in this case. The amplitude of the returning current is then practically zero.

Figure 3:
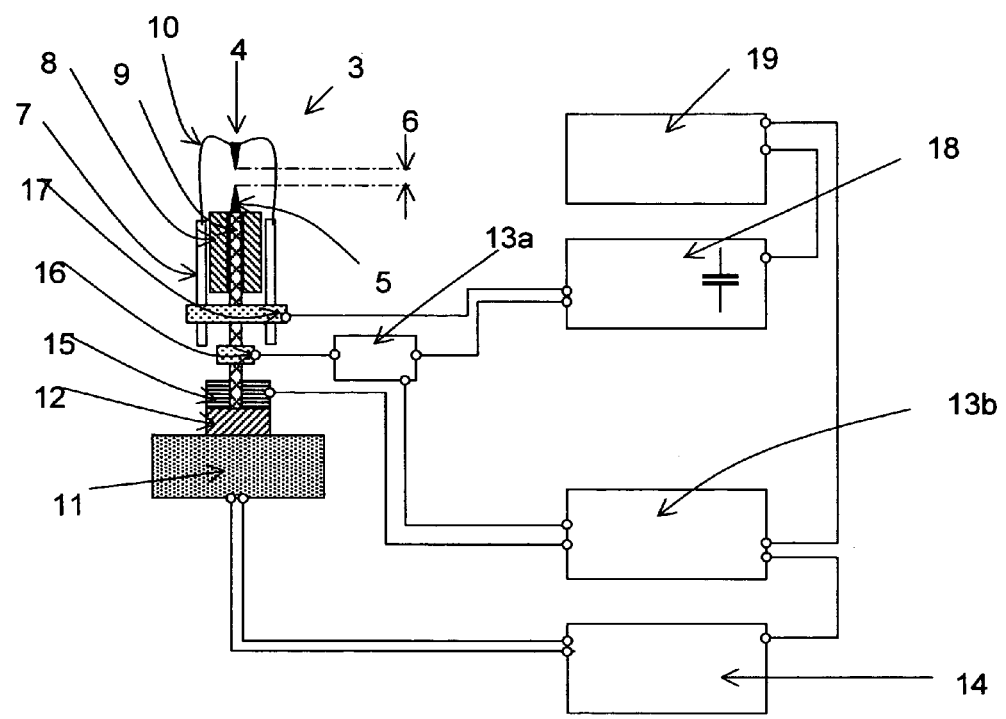
FIG. 3a a block diagram of an exemplary embodiment of an apparatus according to the invention.

FIG. 3a shows a block diagram of an exemplary embodiment of an apparatus according to the invention.

The pressure pulse is generated at an electrode 3, which has two tips 4, 5 between which there is a distance 6.

The electrode comprises an outer conductor 7 and an inner conductor 9 separated by an insulator 8. The electrode tip 4 is connected with the outer conductor 7 by means of an electrode basket made of metal wire 10. The inner conductor 9 can be moved with a motor 11 by means of a transmission 12. If the motor 11 and transmission 12 receive an input signal from a controller 14 via a control unit of a measuring and control apparatus 13b, the inner conductor 9 is set in rotation and moves in a thread not depicted in the drawing that is executed in the insulator 8, depending on the direction of rotation of the motor either toward the electrode tip 4 or away from it. A sensor 15 measures the absolute or relative position of the inner conductor 9 during this movement.

A measuring unit of the measuring and control apparatus 13a measures current between the contact points on the inner conductor 16 and on the outer conductor 17, and therefore between the electrode tips 4, 5.

The pressure wave generation is achieved by applying the voltage of the discharge circuit 18 via the contacts to the inner conductor 16 and to the outer conductor 17. The discharge circuit 18 is supplied by a high-voltage generator 19. The energy is stored in the discharge circuit 18 until the voltage is applied to the contacts 16, 17 by connecting a high-voltage switch, e.g. a spark gap or a thyratron, not depicted in the drawing. After each discharge the discharge circuit 18 is again charged to the selected voltage by the high-voltage generator 19. For safety reasons the outer conductor of the electrode 7 is frequently grounded.

In a first operational variant the control unit of the measuring and control device 13b compares the measured current values and the voltage value with one or more set values and then sends a signal for adjusting the electrode distance 6. In a second operational variant the distance 6 remains constant. The control unit of the measuring and control device 13b sends a signal to the high-voltage generator 19 for selection of the applied voltage.

The measuring unit 13a and the control unit 13b of the measuring and control device can be designed separately, as indicated in this block diagram, or in one component.

I claim:

1. Apparatus for optimized electro-hydraulic pressure pulse generation; comprising an electro-hydraulic shock wave system wherein said shock wave system is equipped with a measuring and control device which measures a discharge current and corrects changing system parameters during normal use between at least two electrode tips, and further which determines if the current measurement results indicate that the pressure pulse generation is taking place in a selected oscillation range and a system parameter correction is made after each discharge based upon the determination and for each treatment the total number of discharges released is able to stabilize the shock wave system due to successive execution of the system parameter changes during normal operation.

2. Apparatus as claimed in claim 1, wherein the measuring and control device measures a discharge voltage.

3. A method for extra-corporeally disintegrating concretions in human beings and other mammals comprising
   administering to a human being or other mammal having at least one concretion at least one electro-hydraulic shock wave, wherein said shock wave is delivered by the apparatus of claim 2.

4. An extra-corporeal treatment method for treating at least one tissue of a human or other mammal comprising
   administering to said tissue at least one electro-hydraulic shock wave, wherein said shock wave is delivered by the apparatus of claim 2.

5. Apparatus as claimed in claim 2, wherein the measuring and control device defines a discharge output.

6. Apparatus as claimed in claim 2, wherein the measuring and control device compares at least one measured or control value with at least one set value.

7. Apparatus as claimed in claim 2. wherein an electrode distance between said electrode tips is variable.

8. Apparatus as claimed in claim 6, wherein
   in case of deviation of at least one measured or control value from at least one set value, or
   in case or deviation of measured and control value curves from set value curves, the measuring and control device corrects the electrode distance.

9. Apparatus as claimed in claim 2, wherein
   in case of deviation of at least one measured or control value from at least one set value, or
   in case of deviation of measured and control value curves from set value curves, the measuring and control device corrects a charging voltage.

10. Apparatus as claimed in in claim 1, wherein the measuring and control device defines a discharge output.

11. A method for extra-corporeally disintegrating concretions in human beings and other mammals comprising
    administering to a human being or other mammal having at least one concretion at least one electro-hydraulic shock wave, wherein said shock wave is delivered by the apparatus of claim 10.

12. An extra-corporeal treatment method for treating at least one tissue of a human or other mammal comprising
    administering to said tissue at least one electro-hydraulic shock wave, wherein said shock wave is delivered by the apparatus of claim 10.

13. Apparatus as claimed in claim 10, wherein the measuring and control device compares at least one measured or control value with at least one set value.

14. Apparatus as claimed in claim 10, wherein an electrode distance between said electrode tips is variable.

15. Apparatus as claimed in claim 14, wherein
in case of deviation of at least one measured or control value from at least one set value, or
in case of deviation of measured and control value curves from set value curves, the measuring and control device corrects the electrode distance.

16. Apparatus as claimed in claim 10, wherein
in case of deviation of at least one measured or control value from at least one set value, or
in case of deviation of measured and control value curves from set value curves, the measuring and control device corrects a charging voltage.

17. Apparatus as claimed in that in claim 1, wherein the measuring and control device compares at least one measured or control value with at least one set value.

18. A method for extra-corporeally disintegrating concretions in human beings and other mammals comprising
administering to a human being or other mammal having at least one concretion at least one electro-hydraulic shock wave, wherein said shock wave is delivered by the apparatus of claim 17.

19. An extra-corporeal treatment method for treating at least one tissue of a human or other mammal comprising
administering to said tissue at least one electro-hydraulic shock wave, wherein said shock wave is delivered by the apparatus of claim 17.

20. Apparatus as claimed in claim 17, wherein an electrode distance between said electrode tips is variable.

21. Apparatus as claimed in claim 20, wherein
in case of deviation of at least one measured or control value from at least one set value, or
in case of deviation of measured and control value curves from set value curves, the measuring and control device corrects the electrode distance.

22. Apparatus as claimed in claim 17, wherein
in case of deviation of at least one measured or control value from at least one set value, or
in case of deviation of measured and control value curves from set value curves, the measuring and control device corrects a charging voltage.

23. Apparatus as claimed in claim 1, wherein an electrode distance between said electrode lips is variable.

24. Apparatus as claimed in claim 23 wherein
in case of deviation of at least one measured or control value from at least one set value, or
in case of deviation of measured and control value curves from set value curves, the measuring and control device corrects the electrode distance.

25. A method for extra-corporeally disintegrating concretions in human beings and other mammals comprising
administering to a human being or other mammal having at least one concretion at least one electro-hydraulic shock wave, wherein said shock wave is delivered by the apparatus of claim 24.

26. An extra-corporeal treatment method for treating at least one tissue of a human or other mammal comprising
administering to said tissue at least one electro-hydraulic shock wave, wherein said shock wave is delivered by the apparatus of claim 24.

27. A method for extra-corporeally disintegrating concretions in human beings and other mammals comprising
administering to a human being or other mammal having at least one concretion at least one electro-hydraulic shock wave, wherein said shock wave is delivered by the apparatus of claim 23.

28. An extra-corporeal treatment method for treating at least one tissue of a human or other mammal comprising
administering to said tissue at least one electro-hydraulic shock wave, wherein said shock wave is delivered by the apparatus of claim 23.

29. Apparatus as claimed in claim 23, wherein
in case of deviation of at least one measured or control value from at least one set value, or
in case of deviation of measured and control value curves from set value curves, the measuring and control device corrects a charging voltage.

30. Apparatus as claimed in claim 1, wherein
in case of deviation of at least one measured or control value from at least one set value, or
in case of deviation of measured and control value curves from set value curves, the measuring and control device corrects a charging voltage.

31. A method for extra-corporeally disintegrating concretions in human beings and other mammals comprising
administering to a human being or other mammal having at least one concretion at least one electro-hydraulic shock wave, wherein said shock wave is delivered by the apparatus of claim 30.

32. An extra-corporeal treatment method for treating at least one tissue of a human or other mammal comprising
administering to said tissue at least one electro-hydraulic shock wave, wherein said shock wave is delivered by the apparatus of claim 30.

33. A method for extra-corporeally disintegrating concretions in human beings and other mammals comprising
administering to a human being or other mammal having at least one concretion at least one electro-hydraulic shack wave, wherein said shock wave is delivered by the apparatus of claim 1.

34. An extra-corporeal treatment method for treating at least one tissue of a human or other mammal comprising
administering to said tissue at least one electro-hydraulic shock wave, wherein said shock wave as delivered by the apparatus of claim 1.

35. Process for the generation of optimized electro-hydraulic pressure pulses characterized by the following process steps:
a) Setting a RLC circuit and an electrode distance in an electro-hydraulic shock wave system to selected initial parameters,
b) Initiating a discharging process,
c) Determining a discharge current during normal use and at least one measured value by a measuring and control device,
d) Comparing the discharge current with at least one set value to determine whether the pressure pulse generation is taking place in a selected oscillation range,
e) Correcting a system parameter by a correction increment based on a deviation from the set value, the correction being made after each discharge to stabilize the discharge process due to successive execution of the system parameter changes during normal operation, and
f) Repeating steps b) through e) to provide a treatment.

* * * * *